United States Patent

Douysset

(10) Patent No.: US 7,488,956 B2
(45) Date of Patent: Feb. 10, 2009

(54) SUPPORT AND POSITIONING SYSTEM FOR MINIATURE RADIOACTIVE SOURCES BY AERODYNAMIC LEVITATION AND APPLICATION TO A DEVICE FOR CONTINUOUS CHARACTERISATION OF PROSTATE IMPLANTS

(75) Inventor: Guilhem Douysset, Viroflay (FR)

(73) Assignee: Commissariat a l'Energe Atomique, Paris (FR)

( * ) Notice: Subject to any disclaimer, the term of this patent is extended or adjusted under 35 U.S.C. 154(b) by 374 days.

(21) Appl. No.: 11/496,453

(22) Filed: Aug. 1, 2006

(65) Prior Publication Data

US 2007/0282153 A1 Dec. 6, 2007

(30) Foreign Application Priority Data

May 16, 2006 (FR) .................................. 06 51757

(51) Int. Cl.
*G01J 1/00* (2006.01)
*A61M 36/00* (2006.01)
*A61N 5/00* (2006.01)

(52) U.S. Cl. ............................. 250/491.1; 600/1; 600/3; 600/7

(58) Field of Classification Search ................. 250/580, 250/393, 491.1; 600/3, 7, 1
See application file for complete search history.

(56) References Cited

U.S. PATENT DOCUMENTS

| 4,378,209 A | 3/1983 | Berge et al. |
| 4,958,126 A * | 9/1990 | Brevard et al. ............... 324/318 |
| 5,095,217 A | 3/1992 | Attix |
| 6,030,013 A | 2/2000 | Fruhling et al. |
| 6,168,638 B1 | 1/2001 | Kasim et al. |
| 2002/0162828 A1 | 11/2002 | Spooner et al. |
| 2004/0034268 A1 | 2/2004 | Dell et al. |

FOREIGN PATENT DOCUMENTS

| EP | 0 337 908 A1 | 10/1989 |
| WO | WO 01/89631 A2 | 11/2001 |

OTHER PUBLICATIONS

Stephen M. Seltzer, et al., "New National Air-Kerma-Strength Standards for $^{125}$I and $^{103}$Pd Brachytherapy Seeds", Journal of Research of the National Institute of Standards and Technology, vol. 108, No. 5, Sep.-Oct. 2003, pp. 337-358.

(Continued)

*Primary Examiner*—David P Porta
*Assistant Examiner*—Carolyn Igyarto
(74) *Attorney, Agent, or Firm*—Oblon, Spivak, McClelland, Maier & Neustadt, P.C.

(57) ABSTRACT

The invention relates to a support and positioning system for at least one miniaturized element in the form of a cylinder. The system comprises a tube comprising an upper part, a median part and a lower part, the upper part being provided with an orifice into which the element is inserted and enabling displacement of the element as far as the median part that has a diameter slightly greater than the diameter of the cylinder forming the element, the lower part being connected to means for controlled injection of a gas to inject a gas inside the tube so as to levitate the element to the required height in the median part of the tube, the lower part of the tube being provided with an element removal orifice, the tube also comprising means of dissipating static electricity inside the tube. Application for characterization of miniaturized radioactive sources.

17 Claims, 2 Drawing Sheets

OTHER PUBLICATIONS

W. S. Culberson, et al., "Large-volume ionization chamber with variable apertures for air-kerma measurements of low-energy radiation sources", Review of Scientific Instruments, vol. 77, 2006, pp. 015105-1 to 015105-9.

* cited by examiner

SUPPORT AND POSITIONING SYSTEM FOR MINIATURE RADIOACTIVE SOURCES BY AERODYNAMIC LEVITATION AND APPLICATION TO A DEVICE FOR CONTINUOUS CHARACTERISATION OF PROSTATE IMPLANTS

TECHNICAL FIELD

The proposed invention relates particularly to a system for supporting and positioning miniature radioactive sources in order to characterise them. This device can be used as a central element of a multi-sensor detector to continuously and completely characterise radioactive implants intended for a number of purposes including brachytherapy of prostate cancers. However, although the invention was designed to characterise radioactive sources, it can be used for other purposes, to levitate a small cylinder made of any material whatsoever.

STATE OF PRIOR ART

Brachytherapy is an attractive alternative to surgery or conventional radiotherapy for the treatment of some cancers. This is true particularly for the treatment of prostate cancers. This type of pathology is now increasing strongly due to early diagnosis.

Brachytherapy by permanent implants consists of irradiating the tumour by placing about a hundred miniature sources of iodine-125 or palladium-103 (iodine-125 being used far more frequently) directly inside the patient's prostate. Implantation is done in a single step under a local anaesthetic. Consequently, the protocol is easier to tolerate for the patient (about thirty sessions are often necessary with external irradiation). This approach also reduces the dose delivered to surrounding healthy tissue compared with external irradiation, while maximizing the dose delivered to the tumour. Isotopes are selected for the low energy of their emission spectrum (from 15 keV to 35 keV) and therefore the weak penetration of their radiation.

Radioactive decay is equally fast (the radioactive half-life of iodine 125 is 59 days and the half-life of palladium-103 is 17 days): a few months, after implantation, the patient's body contains virtually no more radioactive material, therefore the sources are left in place.

This treatment method that has been in use for the last 10 years or so in the USA, showed that the results obtained in tumour checkups were comparable to results obtained with other treatment techniques (surgery, external radiotherapy). The genuine benefit is for side effects. It is now accepted that post-treatment complications were significantly lower with this technique. However, experience shows that this benefit is obtained in full for cancers in the early stages. However, due to systematic screening now applied, a large proportion of cancers are diagnosed in these early stages and in young persons for whom the lack of side effects is an important factor in making the therapeutic choice.

At the present time, almost 230 000 prostate cancers are diagnosed every year in the United States alone. About 100 000 treatments are performed by implants every year. Therefore, brachytherapy is a large market and in a few years about twenty manufacturers have started manufacturing sources. This treatment method is still in the start-up phase in Europe, and particularly in France, but it is considered that it should grow quickly in the next few years.

Sources used have the following main characteristics:
  Low individual radioactive activity (from 3 to 600 MBq, namely a dose rate of 0.1 to 20 µGy/h at 1 m for the iodine-125 isotope). This makes dosimetric measurements relatively difficult (low signal/noise ratio)
  Small dimensions. There are several tens of different types of sources on the market, however they are all cylindrical (diameter between 0.7 and 0.8 mm, height between 4.5 and 5.5 mm). Their mass is of the order of ten milligrams. They are relatively difficult to grip and to handle. The sources are relatively fragile, considering that the claddings are thin (of the order of 50 µm of titanium).
  Low energy of the emitted radiation. This is necessary to confine the delivered dose solely to the region of the tumour. However, this makes the emission spectrum sensitive to the environment: absorption of photons in the cladding, in air, diffusion of photons by surrounding materials, etc. In particular, this leads to very strong angular anisotropy of the emission (up to ±5% variation in the dose for a rotation of 360° around the main axis of the source). Moreover, sources sometimes contain markers based on dense metals (Ag, Au) to facilitate their positioning in radiography. Fluorescence induced by these materials profoundly modifies the emitted spectrum and consequently the delivered dose.

As always in radiotherapy, it is essential to have a very precise knowledge of the dose delivered to the patient: an overdose of a few percent systematically causes complications or relapses. Therefore, before implantation, the therapist and the physician need to have a means of measuring the dosimetric characteristics of the sources to be implanted. Since the number of sources used is important and the measurement is relatively difficult to make, it is frequent that only part of the batch of sources is measured. To achieve this, hospital departments usually have well ionisation chambers (cylindrical shaped detector in which the source is fully inserted, see document [1] mentioned at the end of the description). These instruments are fairly simple in design but they need periodic recalibration by authorised metrology services.

On the other hand, the particular characteristics of sources make specific instrumentation necessary. This instrumentation is developed only in national metrology laboratories. A large part of the difficulty lies in manufacturing the source support device facing the detector. The following tricky compromise has to be made; the source must be held firmly, but without using materials that disturb the emission spectrum. It shall be possible to place the source reproducibly facing the detector, and a means of rotating the source during the measurement is also necessary so as to compensate for anistropy of the emission.

Up to now, national metrology laboratories have been the main players in this field. In the United States, the NIST (National Institute of Standards and Technology) developed a detector several years ago capable of making absolute measurements of doses delivered by these sources. The source support device is relatively basic: the source is held vertical by an adhesive itself adapted to a motor that controls rotation (document [2]). Also in the United States, the accredited dosimetry laboratory at Wisconsin University has also recently developed an instrument. The source is held in position facing the detector by a system with four tight nylon wires, at the centre of which the source is inserted. Rotation is controlled by the two motors to which wires are fixed (document [3]). In Germany, the PTB (Physikalish-Technische Bundesanstalt) recently developed a detector in cooperation with the previous laboratory. The design of the source support device is exactly the same as that used at the NIST.

These three systems have many disadvantages. The first is difficulty of use: the source must be positioned precisely in the device using gripping tools (the sources are too active to be handled by hand). The risk of bad positioning, or even loss of the source, is high. The second disadvantage is the relatively invasive nature of the devices; the emission spectrum of the sources can be significantly disturbed by the support system. Finally, the indisputably serious disadvantage of these systems is their limitation in terms of productivity; sources have to be inserted manually into the devices one by one. This means that they cannot be used to measure a large number of sources quickly.

Furthermore, detectors used in hospital departments (well ionisation chambers) are not suitable for processing a large number of sources. The source on which a measurement is made must be manually inserted into an adapter (for example see document [4]) located in the central part of the detector. The source should then be sterilised after the measurement and before implantation. Consequently, most centres only measure some of the batch that will be implanted.

In order to increase the productivity of detectors, document [5] discloses an automatic system for sorting implants as a function of their dosimetric characteristics. Sources are transported individually, horizontally using a purely mechanical system from a «reservoir», through a ionisation chamber in which the dose rates are measured and finally to a sort system (buckets). According to the authors, several thousand sources can be automatically measured one by one and distributed in different batches. This device is probably satisfactory for a dosimetric measurement, but the massive use of mechanical elements strongly disturbs the emission spectra. Therefore this system can only operate correctly after calibration using a known source with exactly the same configuration as the sources to be sorted. On the other hand, it can never be used for spectroscopic characterisations. The many mechanical systems must also be precisely controlled to prevent any accidental destruction of the sources.

More general contactless support systems for small objects do exist. For example, document [6] presents a contactless gripping and transport device for miniature spherical objects. The proposed system operates based on the principle of aerodynamic levitation. The object is held a few millimeters above a gas injection part in the form of a divergent nozzle by a gas flow. This device is applicable solely to spherical shaped objects, with the main application field being microelectronics. Unlike the case in which the object is cylindrical in shape, the movement created in this case is stable, and significantly simplifies the configuration of the device. The object can be displaced vertically for several millimeters, but the system is not designed for this function.

SUMMARY OF THE INVENTION

The purpose of this invention is to remedy the disadvantages of systems according to prior art.

Its purpose is a support and positioning system for at least one miniaturised element in the form of a cylinder, comprising a tube comprising an upper part, a median part and a lower part, the upper part being provided with an orifice into which the element is inserted and enabling displacement of the element as far as the median part that has a diameter slightly greater than the diameter of the cylinder forming the element, the lower part being connected to means for controlled injection of a gas to inject a gas inside the tube so as to levitate the element to the required height in the median part of the tube, the lower part of the tube being provided with an element removal orifice, the tube also comprising means of dissipating static electricity inside the tube.

Advantageously, the diameter of the upper part of the tube is greater than the diameter of the median part of the tube and it is connected to the median part through a funnel-shaped part.

Advantageously, the diameter of the median part of the tube increases from the lower part of the tube until reaching the upper part of the tube.

The gas injection means may be chosen from among rare gases, air, nitrogen and a mix of nitrogen and oxygen injection means. The gas may be injected through a flowmeter, preferably a mass flowmeter.

The means of eliminating static electricity may comprise an electrically conducting wire arranged inside the tube and connected to the earth. They may also include means of bringing electrical charges opposing the charges supplied by static electricity into the tube. These means of bringing in charges may comprise an electrically conducting wire arranged inside the tube and brought to an electrical potential by which it can produce said electrical charges.

The system may also include a position sensor of the source slaving the gas flow injected inside the tube so as to position said element at the required height.

The invention is particularly applicable to the case in which the miniaturised element is a radioactive source.

Another purpose of the invention is a characterisation device for at least one miniaturised radioactive source, characterised in that it comprises a support and positioning system like that defined above and means of characterisation of the miniaturised element that is a radioactive source.

The characterisation means may comprise at least one device chosen from among a spectrometer, a video camera, a dosimeter, an X-ray tube and the associated sensor.

The device may comprise means of injecting radioactive sources successively into the tube, these injection means injecting each new source to be characterised after the previously injected source has been put in levitation, characterised and ejected from the tube. It may also comprise means of closing off the lower end of the tube to close the tube during levitation and characterisation of the source inserted into the tube and to open the tube to recover the characterised source.

BRIEF DESCRIPTION OF THE DRAWING

The invention will be better understood and other advantages and special features will become clear after reading the following description given as a non-limitative example, accompanied by the appended drawings among which.

DETAILED PRESENTATION OF PARTICULAR EMBODIMENTS

The specification for the system that has been developed comprises the following elements:

Minimum disturbance to the emission spectrum: use of elements with low atomic numbers only (in small thicknesses).

Possibility of precise positioning of the source in all directions.

Possibility of vertical translation of the source within a range of at least 3 cm.

Possibility of processing a large number of sources quickly.

Simplicity of use, intrinsic safety of the device (no risk of bad positioning or loss of source)

The principle of the system that has been developed is to levitate the source by a gas flow. Since the source is cylindrical in shape, the only way of obtaining a stable levitation effect is to place the source in a vertical tube with an inside diameter very slightly greater than the diameter of the source.

The designed system uses the principle of the rotameter but in the inverse manner. Rotameters are instruments commonly used to measure fluid flows. They are composed of a vertical tube with a variable cross-section in which a ball or a needle floats. This ball moves in front of a graduated scale, to a greater extent when the fluid flow is greater.

Figure 1:
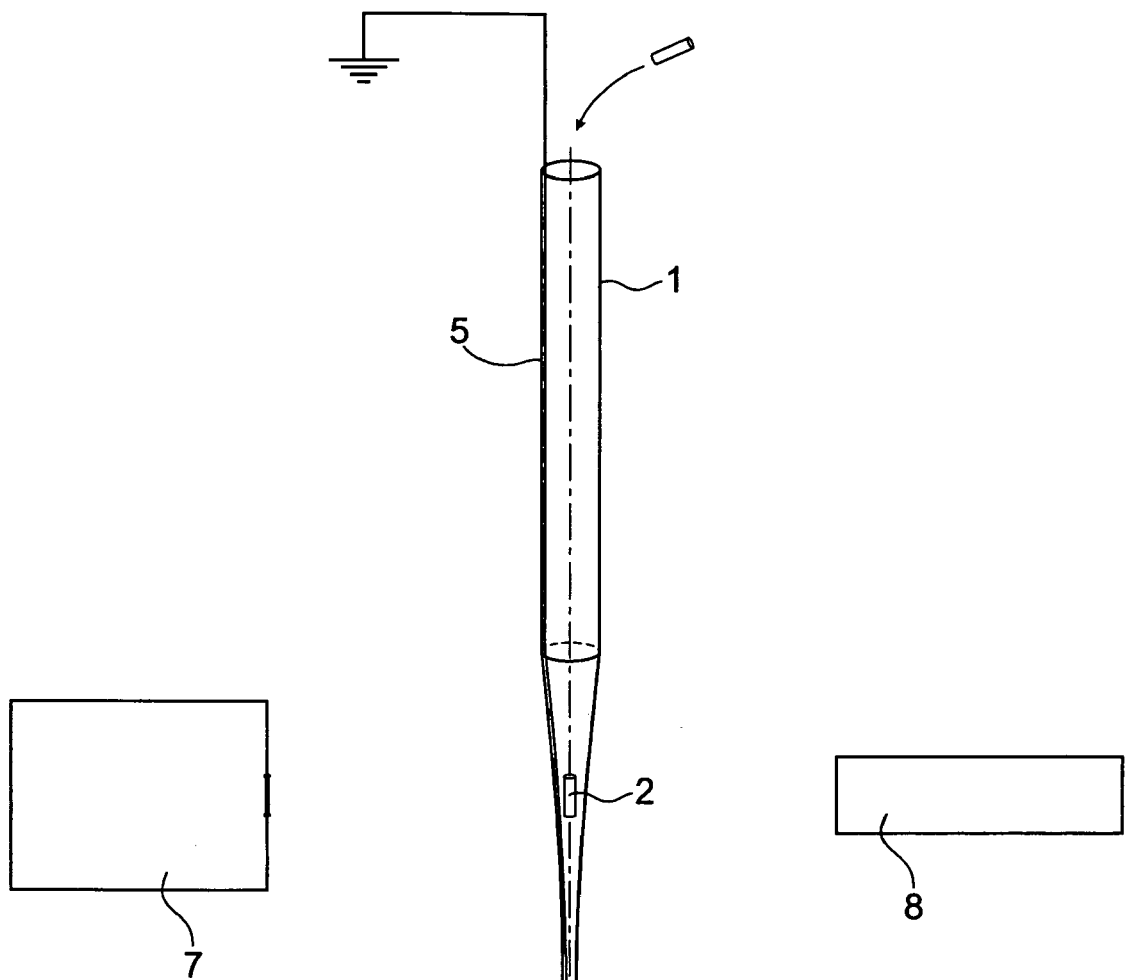
FIG. 1 shows a principle diagram of a device for continuous characterisation of prostate implants according to the invention.

FIG. 1 is a principle diagram of a device for continuous characterisation of prostate implants according to the invention.

This device comprises a cylindrical tube 1 containing the source 2. The tube 1 is supplied with gas from a precision mass flowmeter 3 injecting gas into the lower part of the tube through an adaptor part 4. The tube 1 comprises a lower part with a constant diameter, increasing with increasing distance from the lower part, and a constant diameter upper part. The source 2 is placed at the required height by varying the flow of injected gas. The principle is relatively simple: the weight of the source 2 is compensated by the aerodynamic force due to the injected gas. This force is proportional to the cross-section of the source and the square of the air flow velocity. The gas flow is equal to the product of the flow velocity by the section of the tube and is a conservative magnitude. Therefore, the source 2 is displaced upwards by increasing the blown air flow to compensate for the increase in the diameter of the tube. In practice, gas flows of less than 1 liter per minute are sufficient, considering the low mass of the sources. Due to the cylindrical shape of the source, the movement obtained cannot be stable. The source oscillates laterally at high frequency. However, since the space between the source 2 and the internal wall of the tube 1 is limited, this is of no importance for the dosimetric measurement (the average position remains centred on the tube axis). On the other hand, one primordial advantage of the device is that the source spontaneously rotates about itself. The speed of this rotation depends on the injected flow and is of the order of a few revolutions per second. This provides a very simple means of avoiding the need for mechanized systems used by competitive devices to compensate for anistropy of the emission.

The presented system seems easy to implement at first sight, but in fact difficulties arise. If no special precautions are taken, this system operates for a few minutes and then the source suddenly sticks to the wall of the tube. This sticking is very efficient because it is subsequently very difficult to separate the source. This behaviour is caused by a number of different phenomena. The first and the most obvious is sticking due to capillarity. This type of mechanical sticking can occur if there is the slightest trace of grease on the tube or the sources. Therefore the first precaution to be taken is to clean the elements thoroughly before use (rinsing with an acetone and/or ether solution is sufficient). The same effect can be observed if the injected gas is not perfectly free of grease and water vapour. Therefore, care should be taken to use bottled gas (nitrogen, nitrogen/oxygen 80/20, rare gas, for example argon) that is inherently dry and free of grease. Compressed air can also be used from a central distribution circuit provided that the necessary filtration systems are added to it.

The second phenomenon that explains unwanted sticking is more insidious, and is static electricity. Since the source is in constant collision with the tube, and the tube and the source are electrically isolated, the two elements gradually become charged with static electricity. Since the mass of the sources is very low (about 10 mg), even though the amplitude of the electrostatic force developed is very small, it is sufficient to keep the sources in contact with the wall. It is interesting to note that this phenomenon does not occur with usual rotameters due to their large mass (a few grams) and the shape of the floats used. The effect is also stronger if the inside surface of the tube is a poor conductor. This is precisely the case because the tubes must be thoroughly cleaned, for the reasons mentioned above. The problem is also amplified by the fact that the blown gas is very dry. However, it would be unthinkable to humidify it because the risks of sticking by capillarity would then be too great. Therefore, means of neutralising the charges produced need to be developed to compensate for this effect. This is done by inserting a very thin earthed metallic wire 5 inside the tube (for example with a diameter of between 5 μm and 15 μm). The wire 5 is forced into contact with the wall of the tube. Since the source 2 is in constant collision with the wall of the tube 1, it periodically comes into contact with the wire 5 and can therefore discharge. This device operates perfectly, and once it has been put into place, no more sticking occurs even after several hours of operation. The diameter of the wire 5 is very small and therefore only conceals a very small part of the surface of the source. Moreover, it can be made from a material with a low atomic number (for example Al, Al/Si, carbon fibre) which very much limits disturbance to the photonic spectrum. Another way of neutralising static electricity could also be used; the deliberate addition of electrical charges opposed to spontaneously generated charges. This is done using another small diameter metallic wire, but it is only placed on the inside of the region in which the source is located. This wire is brought to a high voltage (a few thousand volts) and charges are generated at its end by a tip effect. These charges are transported a few centimeters by the gas flow and neutralise the phenomenon. This solution reduces the influence of the wire to zero because the wire is not at the same height as the source, but it is undoubtedly more complex to implement. Furthermore, it is more difficult to apply a measured compensation of charges than to simply neutralise them.

The tube 1 containing the source 2 can be made from any material. However, a transparent material (glass, plastic, quartz, etc.) will be used in preference so as to be able to observe the source 2 directly. The tube can be fabricated based on the model of the sampling pipette (or Pasteur pipette). These pipettes are made by hot drawing from a tube with a constant cross-section. Therefore, they inherently have the variable cross-section necessary for operation of the device. They are flared in the upper part, and the inside diameter is then relatively large (typically between 6 mm and 8 mm). This shape very much facilitates placement of the source in the tube. All that is necessary to activate the gas flow and allow the source to drop into the tube by gravity. The «funnel» shape in the median part of the tube then automatically brings the source to the equilibrium position. Furthermore, since the top diameter of the tube is large, the gas injection mass flowmeter 3 can be chosen such that the maximum blowing flow is too low to cause ejection of the source through the top end of the tube. This significantly improves the safety of the device.

Care will be taken to optimise the thickness and nature of the tube walls so as to minimise absorption of photons and modification of the emission spectrum. For example, a quartz wall ($SiO_2$) of the order of 100 μm in thickness can easily be made and satisfies these constraints: transmission more than 98% at 30 keV and no heavy elements that could cause parasite fluorescence. This tube also filters fluorescence beams from the material making up the cladding of the source (usually titanium). This filtration is necessary to make precise dosimetric measurements. It may also be a good idea to choose a material with a low coefficient of thermal expansion. The equilibrium position of the source would be modified if the inside diameter of the tube changes due to temperature variations.

The entire device presented herein was built and its performances were tested using fictitious radioactive sources. The vertical stability of the source that is one essential parameter was measured: at the moment it is better than ±0.5 mm over several hours. This point could undoubtedly be improved further, particularly by the use of a retro-checking system (optical source position sensor slaving the injected gas flow). However, current performances seem sufficient for the target applications. The resolution of the gas injection mass flowmeter 3 (typically 0.001 l/min) is also sufficient to make very small increments in the vertical displacements (of the order of ±200 μm).

The immediate application of this device relates to absolute dosimetric measurement devices for prostate implants. However, this market is symbolic; potentially, it only concerns a maximum of about ten national metrology laboratories. On the other hand, the developed system has a significant advantage compared with competitive systems, namely it can be automated.

The system is automated by providing a system for injecting sources into the tube one by one. For example, gas can be injected laterally and a controllable valve 6 (or any other element performing the same function) can be added to close off the ejection orifice during levitation of the source. The mass flowmeter must be provided with a control interface (RS232 type).

Such a system can operate according to the following cycle:
  start up gas injection by the flowmeter 3;
  automatic injection of a source 2 into the top part of tube 1;
  adjustment of the gas flow by the flowmeter 3 so as to bring the source 2 into levitation at the height required for the measurement;
  measure characteristics of the source 2 in levitation;
  open the valve and stop gas injection if required, the source then drops by gravity into the lower part of the tube 1 and is led into an adapted receptacle;
  return to the beginning of the cycle for the next source.

With this configuration, a large number of sources can be processed quickly. This satisfies an industrial need. The world annual production of sources is more than 10 million units per year. These sources are produced industrially by automatic machines of the type divulged in document [7]. Experience shows that the production quality is variable. Manufacturing of these sources is difficult due to their small size and a large disparity between batches produced is often observed; some sources are too active, others are not at all active, and dimensional disparities or non-uniformity problems exist.

With the device described, a multi-sensor detector can be manufactured capable of completely characterising the sources produced. This instrument would be modest in size (order of magnitude—cylinder with a height of 30 cm and an outside diameter of 30 cm), the source support device being located at the centre. Different instruments such as a spectrometer 7, a video camera 8, a dosimeter or even a miniature X-ray tube and its associated sensor can be placed around the source (these elements are not shown in FIG. 1). Note that this multi-sensor system would not be possible without the use of the source support device described herein.

The purpose of the spectrometer 7 is to characterise the emission spectrum of sources (verification of activity, the presence of markers, the nature of any pollutants). The distribution of radioactivity within the source can also be measured by using an adapted collimator and displacing the source 2 vertically. Compact spectrometers that do not need cooling by liquid nitrogen are now available on the market and are suitable for this application.

The video camera 8 displays the source 2. A magnification of 20 to 50 can easily be achieved if an appropriate objective is used. This makes it possible to check the condition of the source surface (weld quality, appearance of the cladding, etc.). A dimensional check can also be carried out using image processing software. The mass of the source can also be deduced from these measurements with good sensitivity, knowing the injected gas flow and the dimensions and position of the source. Adapted miniature cameras are available on the market.

A dosimeter assures the emitted dose rate. It is simply a transfer instrument (therefore requiring calibration) and not an absolute sensor.

Finally, an image of the inside of the source can be produced using the X-ray tube and an adapted sensor. This image is useful to make a judgement about the manufacturing quality (cladding thickness, position of markers, etc.). This can also be done by autoradiography, the radioactive source itself replacing the X-ray tube.

Finally, a source sorting system based on the results obtained from the different sensors can be added to the assembly. Nonconform sources can thus be separated and sources can be sorted as a function of the emitted dose rate. It is estimated that a source can be completely characterised in about ten seconds, which corresponds to 3 600 sources measured per day (in other words 10 hours), or a million sources per year (in other words 300 days).

Figure 2:
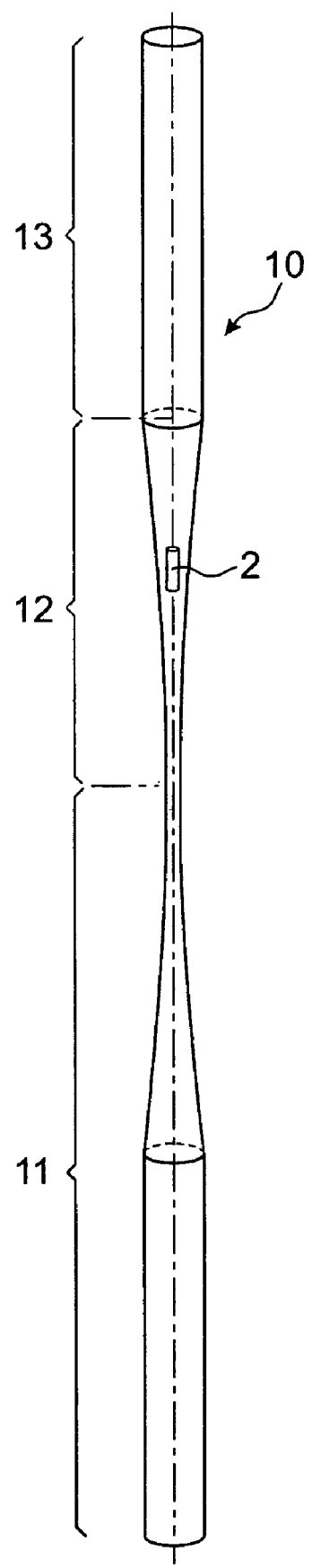
FIG. 2 shows a variant of the tube that can be used for this invention.

FIG. 2 shows another tube that can be used with this invention. The tube 10 comprises a lower part 11, a median part 12 and an upper part 13. The diameter of the lower part 11 decreases before its junction with the median part 12. The diameter of the part 12 increases from its junction with the lower part 11 to its junction with the upper part 13. The diameter of the upper part 13 is constant. The source 2 is shown at the height required to characterise it.

The first clients of this type of instrument could be source manufacturers (there are about twenty in the world) who would like to characterise the quality of their production and optimise their manufacturing process.

A simplified version (fewer types of sensors) of this type of instrument could also be developed. This instrument could be useful to practitioners and would actually concern a much wider market. A simple instrument comprising the spectrometer alone or the dosimeter alone could be used to characterise 100% of sources before implantation, in a very short time (about 20 to 30 minutes). This would provide an undeniable benefit for the quality of care. It would also be possible to adapt the system described herein as a source support insert for a conventional well ionisation chamber. By making a simple adaptation to the associated instrumentation, the proposed system could also automate dosimetric measurements of a complete batch of prostate implants. It is also interesting to emphasise that the instrument described in US patent application 2004/0034268 could also be improved (certainly simplified) by use of the device described in this invention.

DOCUMENTS MENTIONED IN THE DESCRIPTION

[1] U.S. Pat. No. 5,095,217.
[2] «New National Air-Kerma-Strength Standards for $^{125}$I and $^{103}$Pd Brachytherapy Seeds »,S. M. Seltzer et al., J. Res. Natl. Inst. Stand. Technol. 108, 337-358 (2003).
[3] «Large-volume ionization chamber with variable apertures for air-kerma measurements of low-energy radiation sources »,W. S. culberson et al., Rev. Sci, Instrum. 77, 015105 (2006).
[4] WO-A-01/89631
[5] US patent application 2004/0034268
[6] U.S. Pat. No. 6,030,013
[7] US patent application 2002/0162828

The invention claimed is:

1. Support and positioning system for at least one miniaturised element in the form of a cylinder, comprising a tube comprising an upper part, a median part and a lower part, the upper part being provided with an orifice into which the element is inserted and enabling displacement of the element as far as the median part that has a diameter slightly greater than the diameter of the cylinder forming the element, the lower part being connected to means for controlled injection of a gas to inject a gas inside the tube so as to levitate the element to the required height in the median part of the tube, the lower part of the tube being provided with an element removal orifice, the tube also comprising means of dissipating static electricity inside the tube.

2. System according to claim 1, wherein the upper part of the tube has a larger diameter than the diameter of the median part of the tube and is connected to the median part through a funnel-shaped part.

3. System according to claim 1, wherein the diameter of the median part of the tube increases from the lower part of the tube until reaching the upper part of the tube.

4. System according to claim 1, wherein the gas injection means are chosen from among rare gases, air, nitrogen and a mix of nitrogen and oxygen injection means.

5. System according to claim 1, wherein the means of eliminating static electricity comprise an electrically conducting wire arranged inside the tube and connected to the earth.

6. System according to claim 5, wherein the electrically conducting wire is made from a material chosen from among Al, Al/Si and carbon fibre.

7. System according to claim 1, wherein the means of eliminating static electricity comprise means of bringing electrical charges opposing the charges supplied by static electricity into the tube.

8. System according to claim 7, wherein the means of bringing electrical charges comprise an electrically conducting wire arranged inside the tube and brought to an electrical potential by which it can produce said electrical charges.

9. System according to claim 1, wherein the tube is made of a transparent material.

10. System according to claim 9, wherein the tube is made of quartz.

11. System according to claim 1, wherein the gas injection means comprise a mass flowmeter.

12. System according to claim 1, including a source position sensor slaving the gas flow injected inside the tube so as to position the said element at the required height.

13. System according to claim 1, wherein the miniaturised element is a radioactive source.

14. Characterisation device for at least one miniaturised radioactive source, comprising a support and positioning system according to claim 13 and means of characterisation of the radioactive source.

15. Device according to claim 14, wherein the characterisation means comprise at least one device chosen from among a spectrometer, a video camera, a dosimeter, an X-ray tube and the associated sensor.

16. Characterisation device for miniaturised radioactive sources according to claim 14, comprising means of injecting radioactive sources successively into the tube, these injection means injecting each new source to be characterised after the previously injected source has been put in levitation, characterised and ejected from the tube.

17. Device according to claim 16, also comprising means of closing off the lower end of the tube to close the tube during levitation and characterisation of the source inserted into the tube and to open the tube to recover the characterised source.

* * * * *

UNITED STATES PATENT AND TRADEMARK OFFICE
CERTIFICATE OF CORRECTION

PATENT NO. : 7,488,956 B2 Page 1 of 1
APPLICATION NO. : 11/496453
DATED : February 10, 2009
INVENTOR(S) : Douysset It is certified that error appears in the above-identified patent and that said Letters Patent is hereby corrected as shown below:

On the title page, Item (73), the Assignee information is incorrect. Item (73) should read:

--(73) Assignee: Commissariat a l'Energie Atomique
Paris (FR)--

Signed and Sealed this

Thirty-first Day of March, 2009

JOHN DOLL
*Acting Director of the United States Patent and Trademark Office*